United States Patent [19]
Kalopissis et al.

[11] 3,954,882
[45] May 4, 1976

[54] NON-IONIC SURFACE-ACTIVE AGENTS DERIVED FROM FATTY CHAIN DIOLS

[75] Inventors: Grégoire Kalopissis, Paris; Guy Vanlerberghe, Mitry-Mory, both of France

[73] Assignee: L'Oreal, Paris, France

[22] Filed: Feb. 12, 1975

[21] Appl. No.: 549,302

Related U.S. Application Data

[60] Division of Ser. No. 279,050, Aug. 9, 1972, Pat. No. 3,880,766, which is a continuation-in-part of Ser. No. 652,005, July 10, 1967, abandoned.

[30] Foreign Application Priority Data

July 12, 1966 Luxemburg.............................. 51542

[52] U.S. Cl........................... 260/613 B; 260/615 B; 424/70; 252/315
[51] Int. Cl.²........................................... C07C 43/20
[58] Field of Search...................... 260/613 B, 615 B

[56] References Cited
UNITED STATES PATENTS

| | | | |
|---|---|---|---|
| 3,578,719 | 5/1971 | Kalopissis et al............ | 260/613 B X |
| 3,708,364 | 1/1973 | Kalopissis et al................. | 252/156 |

FOREIGN PATENTS OR APPLICATIONS

| | | | |
|---|---|---|---|
| 1,180,973 | 2/1970 | United Kingdom............. | 260/615 B |

*Primary Examiner*—Bernard Helfin
*Attorney, Agent, or Firm*—Cushman, Darby & Cushman

[57] ABSTRACT

Non-ionic surface-active agents having the formula:

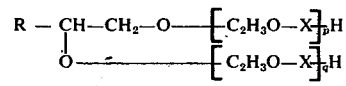

in which R is alkyl, alkenyl, alkoxyalkyl and alkaryloxyalkyl, having 8 to 22 carbon atoms, X represents a $CH_2OH$ or $CH_2O-CH_2-CHOH-CH_2OH$ group, $p$ and $q$ each independently represent a number between 0 and 10 inclusive with the proviso that the sum of $p$ and $q$ is between 1 and 10 inclusive, and methods for preparing said surface-active agents comprising the step of polycondensing $n$ molecules of glycerol epihalohydrin or allylglycidylether with a α-diol having the formula:

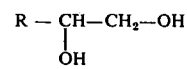

hydroxylating the resulting condensate and subjecting the resulting hydroxylated product to ethanolysis.

1 Claim, No Drawings

NON-IONIC SURFACE-ACTIVE AGENTS DERIVED FROM FATTY CHAIN DIOLS

This is a division of application Ser. No. 279,050 filed Aug. 9, 1972 and now U.S. Pat. No. 3,880,766, which is a continuation-in-part of Ser. No. 652,005, filed July 10, 1967, now abandoned.

There are a large number of non-ionic surface-active agents available, the composition and properties of which are quite varied. However, none of these known agents made from currently available raw materials have all of the characteristics required for a considerable number of applications.

Thus, for example, in the case of ethylene oxide derivatives an increase in the cloud point to 100°C or more results in a very marked decrease in their effectiveness as wetting agents or detergents.

Polyhydroxylated non-ionic surface-active agents are also well known. These surface-active agents are usually prepared by reacting a lipophilic compound with hydrosoluble polyols or sugars. This process produces mixtures of constituents having one or more lipophilic chains per molecule which must be subjected to onerous purifying steps when these products are to be used for purposes which require complete solubility in water.

By introducing hydrophilic substituents on the hydrocarbon chain or adding ethylene oxide to the free hydroxyl groups, the solubility of these compounds in water may be improved.

But because they consistently comprise an ester bond between the lipophilic chain and the hydrophilic component, the resulting compounds are easily hydrolysed in an alkaline medium.

The purpose of the present invention is to provide non-ionic surface-active agents which are both stable and soluble in water at high temperatures even in the presence of electrolytes and which agents have very valuable surface-active properties.

More particularly, one embodiment of the present invention is directed to a method for preparing non-ionic surface-active agents having the formula:

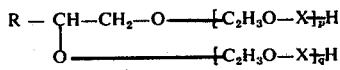

wherein R is selected from the group consisting of alkyl, alkenyl, alkoxyalkyl and alkylaryloxyalkyl, having 8 – 22 carbon atoms, X is —CH$_2$OH, $p$ and $q$ each independently represent a number between 0 and 10 inclusive, with the proviso that the sum of $p$ and $q$ is between 1 and 10 inclusive, the steps comprising 1. condensing on an α-diol having the formula:

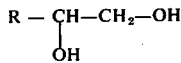

wherein R has the meaning given above, $n$ molecules of glycerol epihalohydrin where $n$ is equal to the sum of $p$ and $q$ defined above, at a temperature ranging from 25°– 160°C in the presence of an acid catalyst selected from the group consisting of boron fluoride, stannic chloride and antimony pentachloride, 2. hydroxylating the resulting condensate from (1) in the presence of an alkaline carboxylic acid salt as an hydroxylating agent at a temperature between 130°– 230°C, and 3. subjecting the resulting hydroxylated product from step (2) to ethanolysis thereby producing said non-ionic surface-active agent.

Another embodiment of the present invention relates to a method for preparing non-ionic surface-active agents having the formula:

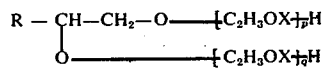

wherein R is selected from the group consisting of alkyl, alkenyl, alkoxyalkyl, alkaryloxyalkyl, having 8 – 22 carbon atoms, X is CH$_2$OCH$_2$—CHOH—CH$_2$OH, $p$ and $q$ each independently represent a number between 0 and 10 inclusive, with the proviso that the sum of $p$ and $q$ is between 1 and 10 inclusive, the steps comprising 1. condensing on an α-diol having the formula:

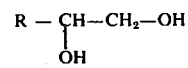

wherein R has the meaning given above, $n$ molecules of allyl glycidyl ether where $n$ is equal to the sum of $p$ and $q$ defined above, at a temperature ranging from 25°– 160°C in the presence of (1) an acid catalyst selected from the group consisting of boron fluoride, stannic chloride and antimony pentachloride, or (2) a basic catalyst such as triethylamine, 2. hydroxylating the resulting condensate from step (1) in the presence of an organic per acid as an hydroxylating agent at a temperature between 20°–80°C, and 3. subjecting the resulting hydroxylated product from step (2) above to ethanolysis thereby producing said non-ionic surface-active agent.

Yet another embodiment of the present invention is the provision of non-ionic surface-active agents having the formula:

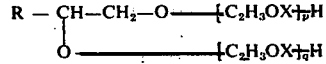

wherein R is selected from the group consisting of alkyl, alkenyl, alkoxyalkyl, and alkylaryloxyalkyl, having 8 – 22 carbon atoms, X is —CH$_2$OH, $p$ and $q$ each independently represent a number between 0 and 10 inclusive, with the proviso that the sum of $p$ and $q$ is between 1 and 10 inclusive, and that $q$ is other than zero when R has 8 – 12 carbon atoms and $p$ is one.

Still another embodiment of the present invention is the provision of non-ionic surface-active agents having the formula:

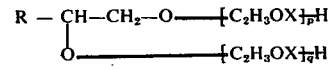

wherein R is selected from the group consisting of alkyl, alkenyl, alkoxyalkyl, or alkylaryloxyalkyl, having 8 – 22 carbon atoms, X is —CH$_2$O CH$_2$—CHOH—CH$_2$OH, $p$ and $q$ each independently represent a number between 0 and 10 inclusive, with the proviso that the sum of $p$ and $q$ is between 1 and 10 inclusive.

In the production of the non-ionic surface-active agents in accordance with the process of the present invention, after completion of the condensation step and before hydroxylation, intermediate compounds of the following formula are produced.

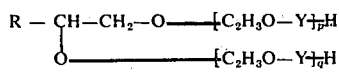

wherein R, $p$ and $q$ have the meaning given above and Y represents $CH_2Z$ or $CH_2OCH_2—CH=CH_2$ wherein Z is a halogen.

During the condensation reaction which comprises the first step of the process according to the invention, a mixture of compounds, all of which respond to the formula for said intermediate compounds described above is formed. For each of these the total number of $[C_2H_3O — Y]$ groups attached to the two alcohol functions of the $\alpha$-diol employed may be greater or less than the statistical average value of the number of molecules of alkyl-glycidyl-ether or glycerol epihalohydrin used per molecule of $\alpha$-diol. The process according to the invention thus makes it possible to obtain a mixture of compounds in which the importance of the hydrophilic chains is dependent on the value of the sum $(p+q)$ of the parameters $p$ and $q$, the group of values of $(p+q)$ being statistically distributed about an average value corresponding to the number of molecules used per molecule of alcohol. But the important fact which should be emphasized and which leads to one of the essential advantages of the process of preparation according to the invention is that this process leads to the formation of compounds having a single lipophilic chain for each hydrophilic chain. The result is that the hydrophilic property of the resulting mixture is greatly increased.

It should moreover be noted that the process according to the invention makes it posible to regulate at will both the hydrophilic and lipophilic properties of the product obtained. In effect, the hydrophilic property of the compounds may be regulated by selecting the value of the number of molecules which are condensed with each molecule of $\alpha$-diol, and their lipophilic property may be regulated by selecting the length and nature of the hydrocarbon or other lipophilic chain of the $\alpha$-diol used to produce the non-ionic surface-active agent.

These $\alpha$-diols may be prepared by hydroxylation, in accordance with known processes, from long-chain $\alpha$-olefins, in pure form or in commercial mixtures.

The process according to the invention is also applicable to hydroxyl compounds having mixed functions such as the alkoxy-alkanediols or the alkyl-aryl-oxyalkanediols. These include the glycerol monoethers such as the lauryl-, tetradecyl-hexadecyl-, octadecyl-, octadecenyl-, octylphenyl-, and nonylphenyl-monoethers of glycerol.

In accordance with the process of the present invention the condensation reaction may be carried out in the presence of an acid catalyst such as boron fluoride, stannic chloride or antimony pentachloride, or when using allyl glycidylether, in the presence of a base catalyst such as triethylamine. This reaction is carried out at a temperature between 25° and 160°C and preferably between 40° and 100°C.

When glycerol epihalohydrin is reacted during the condensation reaction, the hydroxylation reaction which comprises the second step of the process is based on the reaction of the halogenated derivative, obtained during the condensation reaction, with an alkaline carboxylic acid salt, preferably in a solvent which insures the miscibility of the reagents and the ready separation of the mineral halide formed. This hydroxylation reaction takes place between 130° and 230°C, and preferably about 180°C.

With respect to this hydroxylation step it should be noted that the alkaline salt of carboxylic acid employed may advantageously be an acetate, in stoichiometric proportions, or slightly in excess thereof, i.e. about 10 –15% in excess, relative to the halogenated compounds which participate in the reaction.

When allyl glycidyl ether is reacted during the condensation reaction, hydroxylation is preferably effected by means of an organic peracid formed in situ from hydrogen peroxide and an organic acid such as, for example, acetic acid or formic acid. This reaction is carried out between 20° and 80°C and preferably between 30° and 50°C.

After separation of the mineral halide resulting from the hydroxylation reaction, the partially esterified polyhydroxylated polyether is subjected to alcoholysis by means of acetic acid, preferably with the air of absolute ethyl alcohol, in the presence of an alcoholysis catalyst at ambient temperature.

The resulting non-ionic surface-active agents of this invention may be used as wetting agents, detergents, or foaming agents, They have particularly valuable properties with respect to solubility. They are compatible with aqueous concentrated sodium hydroxide solutions (for example up to 40% by weight), and for this reason have many possible industrial applications, particularly in cleaning, metal descaling, and degreasing operations carried out at high temperatures and in the presence of electrolytes.

It should also be noted that, as compared with non-ionic surface-active agents derived from ethylene oxide and comprising an analagous lipophilic chain, the compounds according to the invention have the advantage of being very effective wetting agents even though they remain soluble in water at high temperatures, even in the presence of electrolytes.

The following table gives several wetting times at 25°C measured according to the "Canvas Disk" method described in J. C. Harris' publication "Detergency Evaluation and Testing". The tests were carried out with solutions containing 1% of the product to be tested in demineralized water.

| Compound subjected to tests | Cloud Point | | Wetting time |
| --- | --- | --- | --- |
| | In distilled water | In salt water (10% NaCl) | |
| (a) R—(OCH$_2$CH$_2$)$_n$—OH with n = 23 R = a lauryl radical | more than 100°C | 81°C | more than 5 minutes |

| Compound subjected to tests | Cloud Point | | Wetting time |
|---|---|---|---|
| | In distilled water | In salt water (10% NaCl) | |

-continued (b) 
$$R-CH-CH_2O-[C_2H_3O(CH_2OH)_p]H$$
$$\quad\ \ |$$
$$\quad\ \ O\ \ \ \ \ \ \ \ \ \ [C_2H_3O(CH_2CH)_q]H$$
with p+q = 3.5  R = alkyl radical comprising 9 to 13 carbon atoms — more than 97.5°C — more than 97.5°C — 20 seconds (c)
$$C_{12}H_{25}-CH-CH_2O-[C_2H_3O(CH_2OH)_p]H$$
$$\quad\ \ \ \ \ \ \ \ \ \ |$$
$$\quad\ \ \ \ \ \ \ \ \ \ O\ \ \ \ \ \ \ \ \ \ [C_2H_3O(C-H_2OH)_q]H$$
with p+q = 3.5 — more than 98°C — more than 98°C — 24 seconds Another object of the invention is to provide a cleansing, a shampoo or a detergent composition essentially characterized by the fact that it contains the surface-active agent of the present invention.

The detergent composition according to the present invention is preferably an aqueous solution or paste containing about 1 to 50% of the surface-active agent of this invention, said composition having a pH of about 3 – 9. This composition may also include products or additives customarily used in such industrial products, as for example, thickening agents, sequestrants, anti-settling agents, etc., mineral oil and ionic or non-ionic surface-active agents other than those of this invention.

In order that the invention may be better understood, the following illustrative examples are given and unless otherwise specified all parts and percentages are by weight.

EXAMPLE 1

Preparation of the non-ionic surface-active agent of the formula:

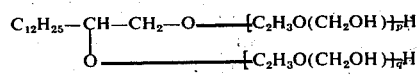

wherein the sum $(p+q)$ has a statistical average value of 3.5.

The starting material is 1,2-tetradecane diol, prepared by hydroxylation of 1-tetradecane by the method described by Swern in "Organic Reactions", Vol. VII at page 399. The 1-tetradecene used to prepare the 1,2-tetradecanediol is a commercial product sold by the Gulf Oil Corporation.

First phase: Condensation reaction 0.20 ml of an acetic composition containing 36% $BF_3$ is added to 34.5 g of distilled $\alpha$-diol having a boiling point of 160°C at a pressure of 1 mm of mercury, which was melted at the moment of use. 48.5 g of glycerol epichlorohydrin are added, while the mixture is agitated. The temperature is kept between 40° and 50°C and the reaction lasts for 45 minutes.

The result is a polychlorinated polyether.

Second phase: Hydroxylation reaction 72 g of the product obtained in this manner are treated with 45 g of potassium acetate, 120 g dipropylene glycol being used as solvent. The hydroxylation reaction is carried out at 180°C and lasts 3 hours. The potassium chloride thus obtained is filtered from the reaction mass.

The dipropylene glycol solvent is then evaporated and the resulting residue is subjected to alcoholysis by adding to the residue 350 ml of absolute ethyl alcohol together with an alcoholysis catalyst consisting of 2.5 g of a solution in methanol containing 25 weight percent of sodium methylate. The resulting alcoholysis reaction mixture is left standing overnight at ambient temperature. Thereafter the alcohol and resulting ethyl acetate are removed thus providing the above defined non-ionic surface-active agent.

This non-ionic surface-active agent is in the form of a very viscous yellow syrup which is easily dissolved in water. Its cloud point, determined for a 0.5% solution, is above 98°C both in distilled water and in salt water containing 10% sodium chloride. This nonionic surface-active agent when mixed with a 30% by weight aqueous solution of sodium hydroxide, gives a paste suitable for descaling metal.

EXAMPLE 2

Preparation of the non-ionic surface-active agent of the formula:

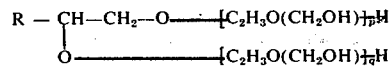

wherein R represents linear alkyl chains having 9 to 13 carbon atoms, the sum $(p+q)$ having a statistical average value of 3.5.

First phase: Condensation reaction

The starting material is an $\alpha$-diol obtained by hydroxylation in accordance with the method described in Swern's "Organic Reactions", Vol. VII, at page 399, beginning with a mixtue of straight chain olefins comprising 11 to 15 carbon atoms and sold commercially under the trademark "Chevron Alpha Olefins", by the Cronite Company.

0.25 ml of an acetic composition containing 36% of $BF_3$, is added to 44 g of a $\alpha$-diol obtained in this manner, which has first been distilled at between 140 and 153°C under a pressure of 1 mm of mercury and melted at the moment of use. 65 g of glycerol epichlorohydrin are then poured in. The reaction lasts 50 minutes, during which the temperature is kept between 40° and 50°C.

This yields a polychlorinated polyether.

Second phase: Hydroxylation reaction

The polychlorinated ether obtained during the first step is hydroxylated with potassium acetate, using dipropylene glycol as a solvent and maintaining the temperature at 180°C for 3 hours. The resulting potassium chloride is filtered, the solvent is evaporated, and after subsequent ethanolysis conducted in a manner essentially as outlined in Example 1, a non-ionic surface-active agent of the formula given at the begging of this Example is obtained. This non-ionic surface active agent is in the form of a yellowish syrup, the cloud point of which in 0.5% solution as described above, has already been given. This product is compatible with aqueous solutions containing 30% by weight of sodium hydroxide. At a concentration of 1% in a 10% sodium hydroxide solution, the product retains its wetting properties (wetting time at 25°C = 140 seconds).

EXAMPLE 3

Preparation of the non-ionic surface-active agent of the formula:

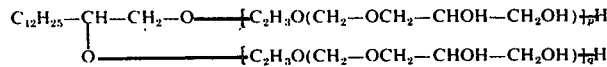

wherein the sum $(p+q)$ has a statistical average value of 1.75.

First phase: Condensation reaction

The starting material used is 1,2 tetra-decanediol prepared by hydroxlizing 1-tetradecene by the method described in Swern's "Organic Reactions", Vol. VII, at page 399. The 1-tetradecene used to prepare the 1,2-tetradecanediol is sold commercially by the Gulf Oil Corporation. 0.1 ml of an acetic composition containing 36% $BF_3$ is added, while stirring, to 27.5 g of 1,2-tetradecanediol distilled at 160°C under a pressure of 1 mm of mercury, and melted at the moment of use. 24 g of allyl glycidyl ether are then added drop by drop while maintaining the temperature at about 60°C. The reaction lasts for about 35 minutes.

Second phase: Hydroxylation reaction 48 g of the product thus obtained are dissolved in 55 g of 98% formic acid and 25 ml of hydrogen peroxide at 116 volumes are then added progressively. After a reaction lasting for 27 hours at 40°C those peroxides formed are destroyed with sodium sulfite and the formic acid is evaporated.

This is followed by ethanolysis essentially as described in Example 1, which results in a colorless semi-solid non-ionic surface-active agent as defined above, which dissolves readily in water and is a good foaming agent. In an 0.5% solution, it has a cloud point above 97°C both in distilled water and in salt water containing 10% sodium chloride.

EXAMPLE 4

Preparation of the non-ionic surface-active agent of the formula:

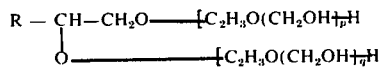

wherein R is an alkyl radical containing 13 to 18 carbon atoms and the sum $(p+q)$ has a statistical average value of 6.

First phase: Condensation reaction

The starting material used is a mixture of $\alpha$-diols obtained by hydroxylizing with hydrogen peroxide, in a medium containing formic acid and ethyl formate, a mixture of olefins comprising 15 to 20 carbon atoms and sold commercially under the trademark "Chevron Alpha Olefins" by the Oronite Company.

0.40 ml of an acetic composition containing 36% $BF_3$ is added to 73 g of $\alpha$-diols recrystallized in petroleum ether and melted at the moment of use. 139 g of glycerol epichlorohydrin are then added drop by drop. The operation takes 45 minutes and the temperature is kept between 60° and 75°C.

The reaction is terminated by adding an additional 0.1 ml of the acetic composition containing boron fluoride, while heating in a boiling water bath for about an hour.

This results in a liquid polychlorinated polyether which is yellow in color.

Second step: Hydroxylation reaction 123.5 g of anhydrous potassium acetate and 0.9 g of potassium borohydride are dissolved in 300 g of dipropylene glycol. The resulting solution is heated to 175°–180°C and 177.5 g of the polychlorinated polyether prepared in the first step is added thereto. After a reaction lasting 3 hours at 180°C the potassium chloride formed is filtered and the solvent is evaporated. The product is de-acetylated by ethanolysis in accordance with the procedures set forth in Example 1.

The resulting non-ionic surface-active agent as defined above is in the form of a paste which is soluble in water. The cloud point in the case of 0.5% solutions, both in distilled water and in salt water containing 10% of sodium chloride, is about 100°C. This non-ionic surface-active agent is soluble in a 40% sodium hydroxide solution.

Several examples of useful compositions including the non-ionic surface-active agent of this invention are given below:

EXAMPLE 5

A gel is prepared in the following manner: To 10 grams of the non-ionic surface-active agent of the formula:

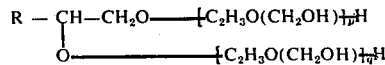

wherein R represents linear alkyl containing 9 to 13 carbon atoms and wherein the sum $(p+q)$ has a statistical average value of 3.5, there are added 10 grams of a 30% soda lye solution. After homogenization, a clear yellow gel is obtained. This composition may be used to clean household ovens and can be applied by means of a damp cloth.

EXAMPLE 6

A gel is prepared by mixing 10 grams of a 30% soda lye solution with 10 grams of a non-ionic surface-active agent of the formula:

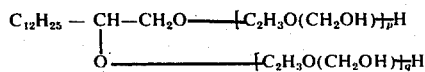

wherein the sum ($p+q$) has a statistical value of 3.5.

After homogenization, a clear yellow gel is obtained which can be used to clean household ovens, the same being applied thereto with a damp cloth.

EXAMPLE 7

A hair shampoo composition is prepared as follows:

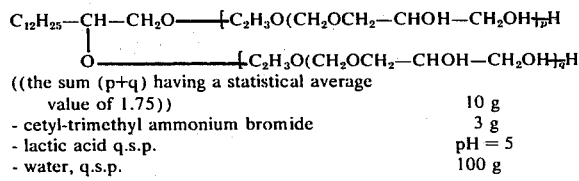

| | |
|---|---|
| ((the sum (p+q) having a statistical average value of 1.75)) | 10 g |
| - cetyl-trimethyl ammonium bromide | 3 g |
| - lactic acid q.s.p. | pH = 5 |
| - water, q.s.p. | 100 g |

10 cm³ of the above shampoo composition is applied to dampened hair which is then vigorously rubbed and thoroughly rinsed with water. A second application of from 8 to 10 cm³ of the above shampoo composition is then effected and a generous lather results. The hair is again rinsed and then dried. The hair is shiny, soft and non-electric.

EXAMPLE 8

A hair shampoo composition is prepared as follows:

$C_{12}H_{25}$—CH—CH$_2$O————$(C_2H_3O(CH_2OCH_2$—CHOH—CH$_2$OH$)_{\overline{p}})$H
 |
 O————$(C_2H_3O(CH_2OCH_2$—CHOH—CH$_2$OH$)_{\overline{q}})$H

| | |
|---|---|
| ((the sum (p+q) having a statistical average value of 1.75)) | 10 g |
| - Copra diethanolamide | 1 g |
| - Polyethylene glycol (molecular weight about 5.000.000) | 0.1 g |
| - Water, q.s.p. | 100 g |

The resulting solution has a pH of 7.5.

For shampooing, the hair is first dampened and then 10 cm³ of the above shampoo composition are applied with vigorous rubbing. The hair is thoroughly rinsed with water and a second application of from 8 to 10 cm³ of the shampoo composition is made. A generous lather results. The hair is rinsed and dried. Hair thus washed is shiny, soft and not electric.

What is claimed is:

1. Non-ionic surface-active agents having the formula:

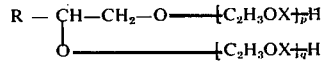

wherein R is selected from the group consisting of alkyl, alkenyl, alkoxyalkyl or alkylaryloxyalkyl, having 8 – 22 carbon atoms, X is —CH$_2$OH, $p$ and $q$ each independently represent a number between 0 and 10 inclusive, with the proviso that the sum of $p$ and $q$ is between 1 and 10 inclusive, and that $q$ is other than zero when R has 8 – 12 carbon atoms and $p$ is 1.

* * * * *